(12) United States Patent
Earl (10) Patent No.: US 8,152,035 B2
(45) Date of Patent: Apr. 10, 2012

(54) RESTRAINING DEVICE FOR A PERCUTANEOUS LEAD ASSEMBLY

(75) Inventor: Nicholas Andrew Earl, Chatswood (AU)

(73) Assignee: Thoratec Corporation, Pleasanton, CA (US)

( * ) Notice: Subject to any disclaimer, the term of this patent is extended or adjusted under 35 U.S.C. 154(b) by 1012 days.

(21) Appl. No.: 11/919,027

(22) PCT Filed: Jul. 6, 2006

(86) PCT No.: PCT/AU2006/000953
§ 371 (c)(1),
(2), (4) Date: May 3, 2008

(87) PCT Pub. No.: WO2007/006080
PCT Pub. Date: Jan. 18, 2007

(65) Prior Publication Data
US 2009/0306492 A1    Dec. 10, 2009

(30) Foreign Application Priority Data
Jul. 12, 2005   (AU) ................ 2005903693

(51) Int. Cl.
*H01R 13/73* (2006.01)
(52) U.S. Cl. ........ 224/267; 224/930; 439/521; 439/905; 439/909
(58) Field of Classification Search ............ 600/386, 600/390, 394; 439/367–373, 909, 521–532, 439/901, 903, 905; 224/267, 271, 929, 930
See application file for complete search history.

(56) References Cited

U.S. PATENT DOCUMENTS

| | | | |
|---|---|---|---|
| 3,834,380 A | 9/1974 | Boyd | |
| 4,143,934 A | 3/1979 | Siebert | |
| 4,206,961 A | 6/1980 | Cifalde | |
| 4,416,664 A * | 11/1983 | Womack | 604/174 |
| 4,480,639 A | 11/1984 | Peterson et al. | |
| 4,579,120 A | 4/1986 | MacGregor | |
| 4,596,430 A | 6/1986 | Olson | |
| 4,643,505 A | 2/1987 | House et al. | |
| 4,723,822 A | 2/1988 | Merdic | |
| 4,906,233 A | 3/1990 | Moriuchi et al. | |
| 5,084,026 A * | 1/1992 | Shapiro | 604/179 |
| 5,129,839 A | 7/1992 | VanSkiver | |
| 5,167,229 A * | 12/1992 | Peckham et al. | 607/48 |
| 5,211,546 A | 5/1993 | Isaacson et al. | |
| 5,211,573 A * | 5/1993 | Cross | 439/369 |
| 5,224,935 A | 7/1993 | Hollands | |
| 5,237,988 A * | 8/1993 | McNeese | 128/207.17 |
| 5,289,821 A | 3/1994 | Schwartz | |
| 5,370,509 A | 12/1994 | Golding et al. | |
| 5,413,562 A * | 5/1995 | Swauger | 604/179 |

(Continued)

FOREIGN PATENT DOCUMENTS

CA    2237203    3/1998
(Continued)

*Primary Examiner* — Lee Cohen
*Assistant Examiner* — Erin M Cardinal
(74) *Attorney, Agent, or Firm* — Squire Sanders (US) LLP (57) ABSTRACT

A device (1) for restraining attached couplers (4, 5) of a percutaneous lead assembly (7). The device (1) comprises a body (14) including two engagement means (8) positioned at opposite ends that engage with the respective couplers (4, 5) to resist disconnection, and an attachment means (9) to attach the device (1) to the outer epidermis of a patient to limit movement of the device (1), when in use.

8 Claims, 9 Drawing Sheets

U.S. PATENT DOCUMENTS

| | | | |
|---|---|---|---|
| 5,443,060 A | 8/1995 | Visceshwara et al. | |
| 5,443,065 A * | 8/1995 | Berghoff et al. | 600/384 |
| 5,593,312 A | 1/1997 | McCracken | |
| 5,681,290 A | 10/1997 | Alexander | |
| 5,695,471 A | 12/1997 | Wampler | |
| 5,810,781 A | 9/1998 | Bierman | |
| 5,840,070 A | 11/1998 | Wampler | |
| 5,876,234 A * | 3/1999 | Hester | 439/369 |
| 5,916,199 A * | 6/1999 | Miles | 604/174 |
| 6,036,525 A | 3/2000 | Alfis, III | |
| D425,619 S | 5/2000 | Bierman | |
| 6,066,086 A | 5/2000 | Antaki et al. | |
| 6,071,093 A | 6/2000 | Hart | |
| 6,080,133 A | 6/2000 | Wampler | |
| 6,100,618 A | 8/2000 | Schoeb et al. | |
| 6,117,086 A * | 9/2000 | Shulze | 600/488 |
| 6,120,537 A | 9/2000 | Wampler | |
| 6,158,984 A | 12/2000 | Cao et al. | |
| 6,217,541 B1 | 4/2001 | Yu | |
| 6,227,797 B1 | 5/2001 | Watterson et al. | |
| 6,234,772 B1 | 5/2001 | Wampler et al. | |
| 6,234,998 B1 | 5/2001 | Wampler | |
| 6,264,635 B1 | 7/2001 | Wampler et al. | |
| 6,368,083 B1 | 4/2002 | Wampler | |
| 6,447,485 B2 | 9/2002 | Bierman | |
| 6,619,975 B2 | 9/2003 | Bentley et al. | |
| 6,623,420 B2 | 9/2003 | Reich et al. | |
| 6,688,861 B2 | 2/2004 | Wampler | |
| 6,689,104 B2 | 2/2004 | Bierman | |
| D495,619 S | 9/2004 | Ward | |
| 6,837,875 B1 | 1/2005 | Bierman | |
| 6,866,625 B1 | 3/2005 | Ayre et al. | |
| 7,284,729 B2 * | 10/2007 | Walsh et al. | 248/74.3 |
| 2001/0009645 A1 | 7/2001 | Noda | |
| 2002/0165493 A1 | 11/2002 | Bierman | |
| 2002/0183628 A1 | 12/2002 | Reich et al. | |
| 2004/0084398 A1 | 5/2004 | Breitschwerdt et al. | |
| 2004/0084399 A1 | 5/2004 | Cook et al. | |
| 2004/0186542 A1 * | 9/2004 | van Venrooij et al. | 607/116 |
| 2004/0199122 A1 | 10/2004 | Bierman et al. | |
| 2004/0234397 A1 | 11/2004 | Wampler | |
| 2005/0085118 A1 | 4/2005 | Robbins | |
| 2007/0129779 A1 * | 6/2007 | Ayre et al. | 607/116 |
| 2007/0231135 A1 | 10/2007 | Wampler et al. | |
| 2008/0080983 A1 | 4/2008 | Wampler et al. | |
| 2008/0085184 A1 | 4/2008 | Wampler et al. | |
| 2008/0089779 A1 | 4/2008 | Wampler et al. | |
| 2008/0089797 A1 | 4/2008 | Wampler et al. | |

FOREIGN PATENT DOCUMENTS

| | | |
|---|---|---|
| DE | 831757 | 7/1952 |
| EP | 0356683 | 3/1990 |
| EP | 1 354 606 | 10/2003 |
| EP | 1475123 | 11/2004 |
| JP | 2002-224066 | 8/2002 |
| JP | 2004-278375 | 10/2004 |
| WO | WO 97/29795 | 8/1997 |
| WO | WO 01/05023 | 1/2001 |
| WO | PCT/AU2006/000953 | 5/2007 |

* cited by examiner

RESTRAINING DEVICE FOR A PERCUTANEOUS LEAD ASSEMBLY

FIELD OF THE INVENTION

The present invention relates to a device for restraining attached couplers of a percutaneous lead assembly.

BACKGROUND OF THE INVENTION

Previously, there have been many devices disclosed that join and prevent disconnection of female and male couplers. Some of these devices are disclosed in U.S. Pat. Nos. 5,129,839—VanSkiver; 4,596,430—Olson; 4,206,961—Cifalde; 4,143,934—Siebert; 6,619,975—Bentley et al; 6,036,525—Alfis III; 4,723,822—Merdic; 4,643,505—House et al; and 5,593,312—McCracken.

However, none of the abovementioned devices have been applied or are suitable to applications for restraining couplers of percutaneous lead assemblies. Percutaneous lead assemblies include leads that are fed through a patient's epidermis and typically power active implantable medical devices. Preferably, these active implantable medical devices include rotary blood pumps such as the devices described in: U.S. Pat. No. 6,227,797—Watterson et al; and U.S. Pat. No. 6,866,625—Ayre et al.

Preferably, percutaneous lead assemblies require the external portion of the lead assembly to be at least partially restrained so as to restrict unnecessary movement of the assembly and the couplers, and none of the aforementioned restrainers or devices achieve this. Unnecessary movement or motion may occur normally during the use of the active implantable medical device or the assembly and may lead to the assembly becoming worn, damaged or accidentally disconnected. Typically, this wear or damage may occur when the percutaneous lead assembly rubs against the outer skin layer or epidermis of the patient. Also, accidental disconnection may occur because of the stresses experienced by the percutaneous lead assembly, when in use. Additionally, the motion of the percutaneous lead assembly, when in use, may accidentally activate the release mechanisms described in the prior art and lead to accidental disconnection of the couplers.

U.S. Pat. No. 4,579,120—MacGregor describes a device for restraining a percutaneous lead by means of a flexible, elastomeric disc having a surface for contacting and conforming to the body of the patient. This device, that does not utilise couplers, has a major disadvantage. If the percutaneous lead is damaged, there is no way a clinician may easily replace the external portions of the lead without surgically cutting the lead from the patient's body. Furthermore, the device does not provide a sufficient strain relief necessary when the percutaneous lead is exposed to normal "wear and tear" conditions.

Whilst there are also many devices for coupling medical devices by utilising couplers, such as cannulation for drug delivery and the like, such couplers are not adapted for restraining these devices against the patient's body.

None of the aforementioned restraining devices are adapted for minimal wear and damage to couplers of a percutaneous lead assembly, nor are they suited to restricting the disconnection of such couplers.

The present invention aims to or at least address or ameliorate one or more of the disadvantages associated with the abovementioned restraining device prior art.

SUMMARY OF INVENTION

According to a first aspect the present invention consists of a device for restraining attached couplers of a percutaneous lead assembly operably connected to a medical device implanted within a patient, wherein said device comprises: a body including two engagement means positioned at opposed ends that engage with the respective couplers to resist disconnection; and an attachment means to attach the device to the outer epidermis of a patient to limit movement of the device, when in use.

Preferably said body includes a cradle to receive the attached couplers.

Preferably each engagement means includes at least one flange for engaging the outer surface of at least one coupler;

Preferably said outer surface of the attached couplers includes at least one slot, which cooperates with at least one flange.

Preferably said attachment means includes at least one flexible strip.

Preferably attachment means includes at least one side mounted extension on the body and wherein said extension includes a gap for receiving said flexible strip.

Preferably said flexible strip is attached to the epidermis of a patient and the device.

Preferably said flexible strip at least partially shields or guards said couplers from damage, when in use.

Preferably in another embodiment the flexible strip comprises a strip of Velcro™.

Preferably said device at least partially shields said couplers.

Preferably said device is for use with an implantable medical device.

Preferably said device is constructed of an Acetal Resin.

According to a second aspect the present invention consists of a method of restraining attached couplers of a percutaneous lead assembly operably connected to a medical device implanted within a patient, wherein said method comprises the steps of: inserting two attached couplers within a cradle and wherein said cradle prevents couplers from being detached without removal from cradle; and attaching said cradle to the epidermis of a patient to prevent movement of cradle.

According to a third aspect the present invention consists of a method for attaching a percutaneous lead assembly operably connected to a medical device implanted within a patient; wherein said method includes the steps of: attaching two couplers which form part of the percutaneous lead assembly; inserting attached couplers within a cradle; cradle engages the attached couplers; and the cradle is attached to the outer epidermis of a patient

BRIEF DESCRIPTION OF THE DRAWINGS

Embodiments of the present invention will now be described with reference to the accompanying drawings wherein.

BRIEF DESCRIPTION OF THE PREFERRED EMBODIMENTS

Figure 1:
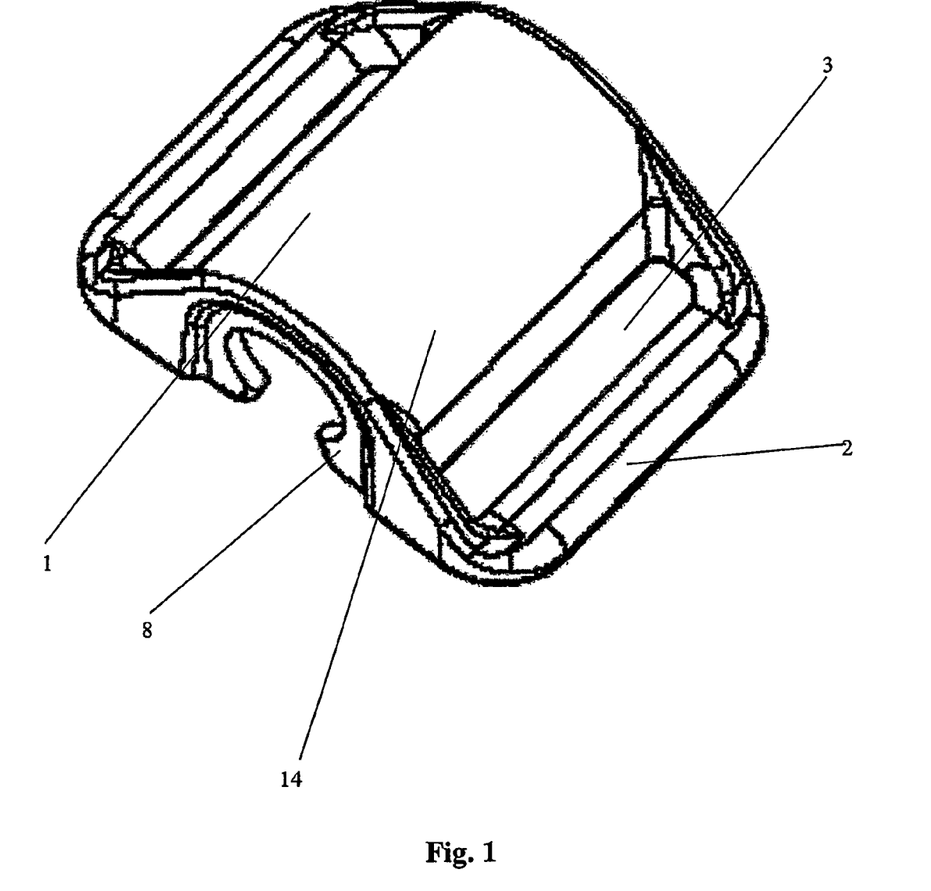
FIG. 1 is a perspective view of a first embodiment of the present invention.
Figure 2:
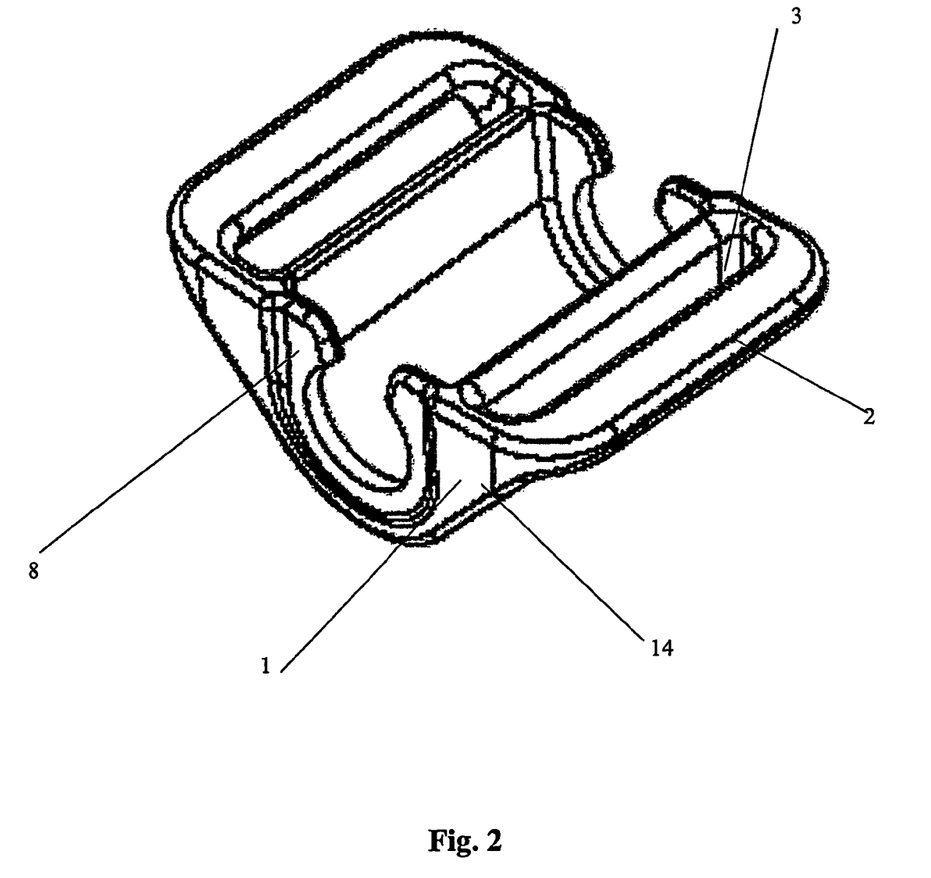
FIG. 2 is an inverted view of the first embodiment as shown in FIG. 1.
Figure 3:
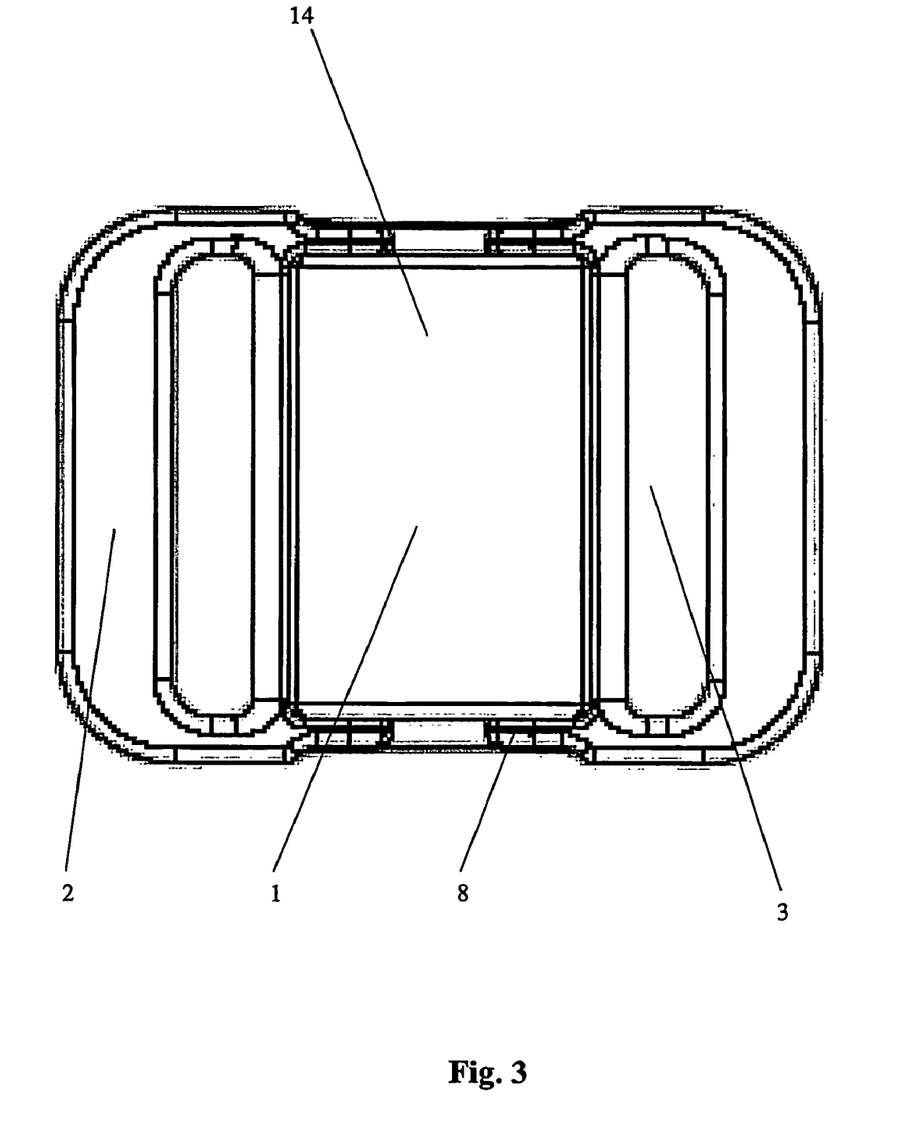
FIG. 3 is bottom view of the first embodiment as shown in FIG. 1.
Figure 4:
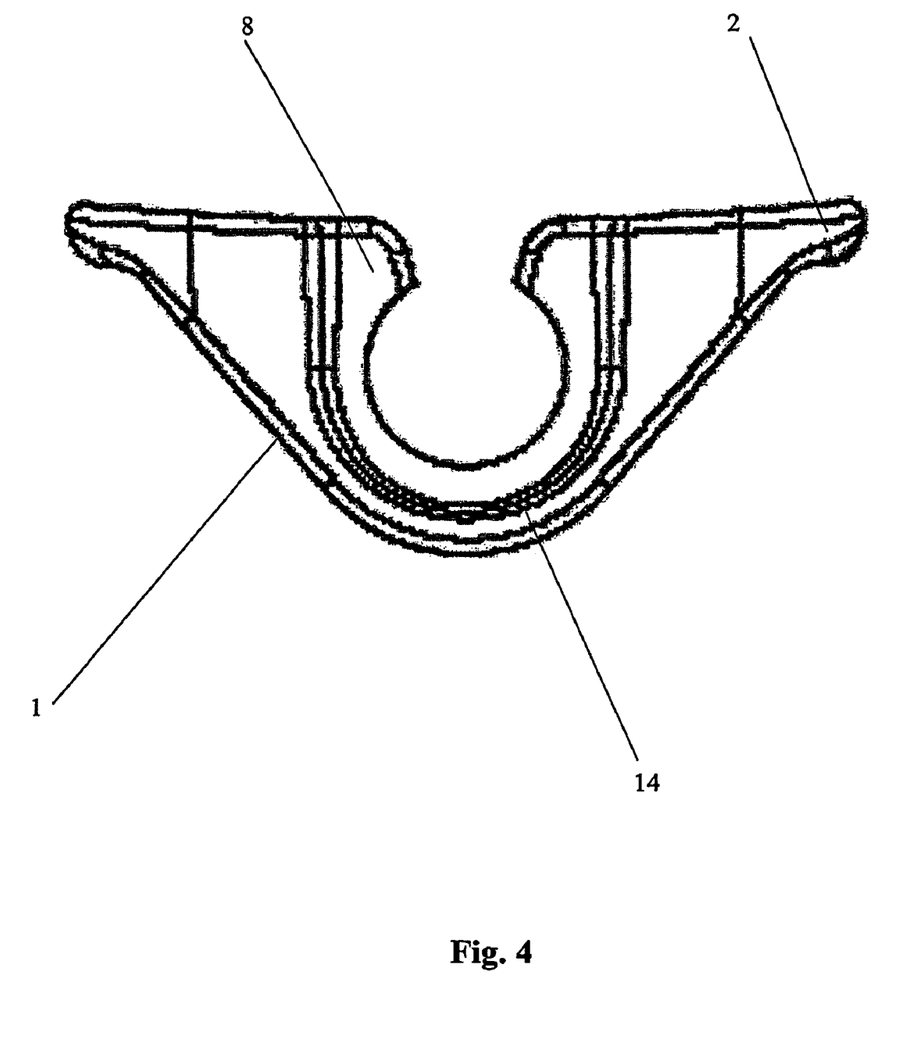
FIG. 4 is an end view of the first embodiment as shown in FIG. 1.
Figure 5:
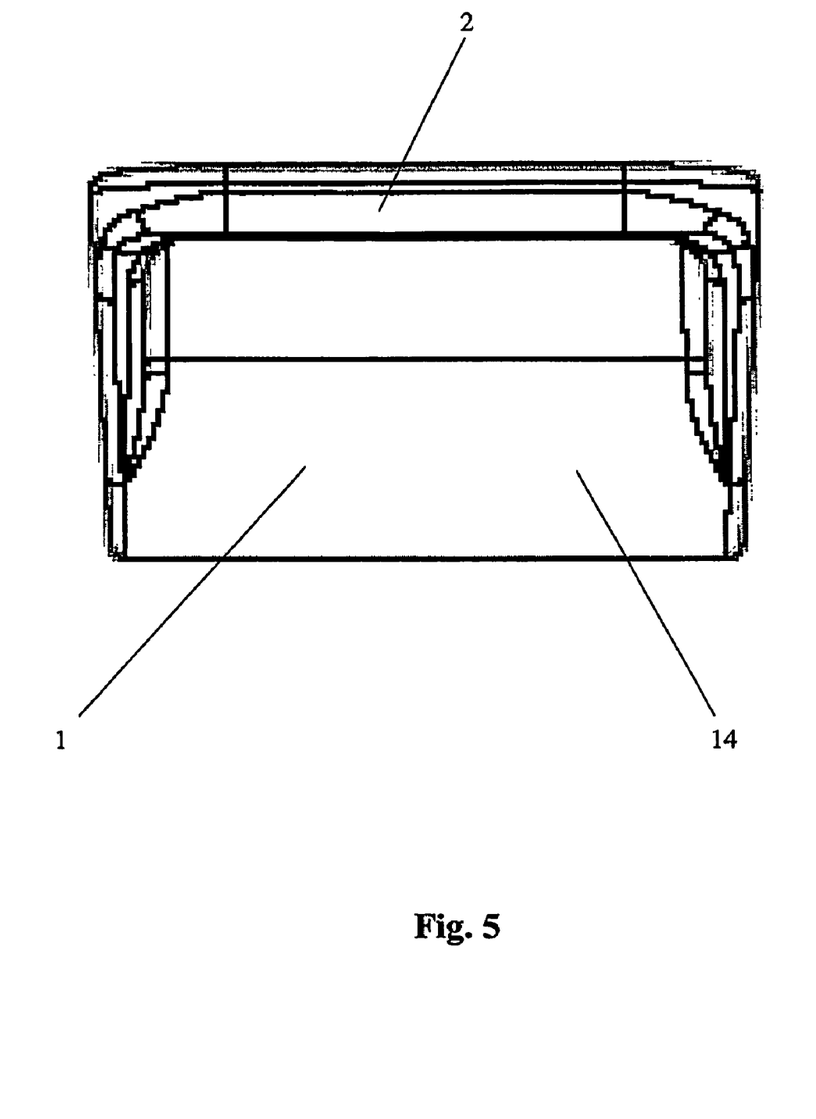
FIG. 5 is a side view of the first embodiment as shown in FIG. 1.
Figure 6:
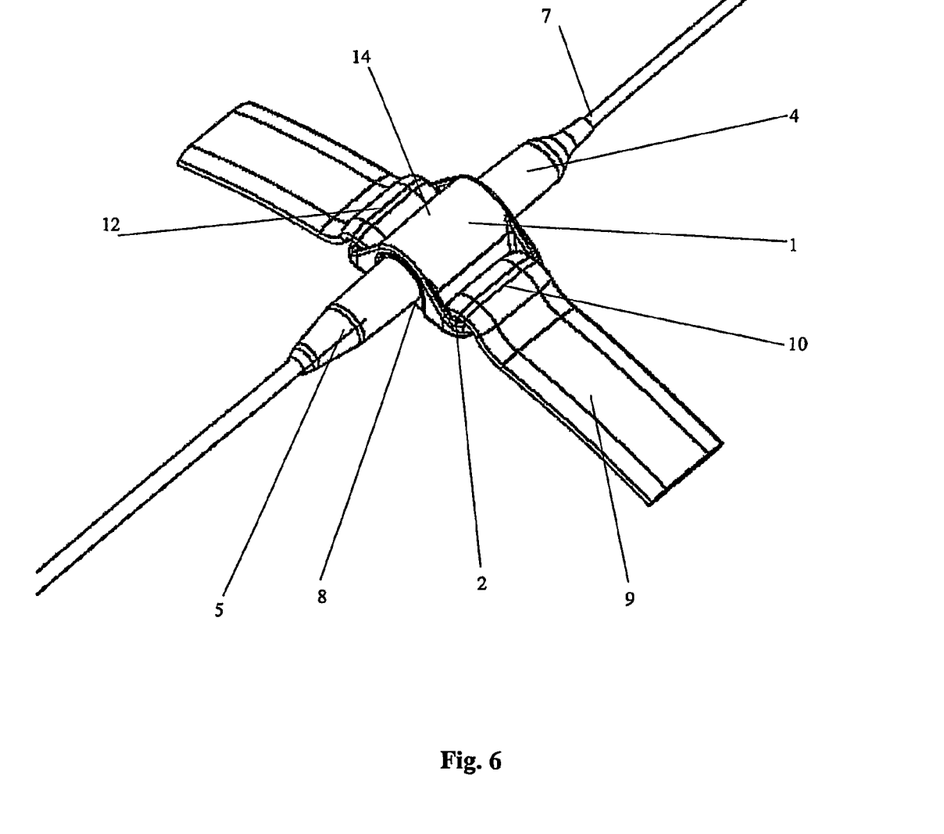
FIG. 6 is a perspective view of the first embodiment in use.
Figure 7:
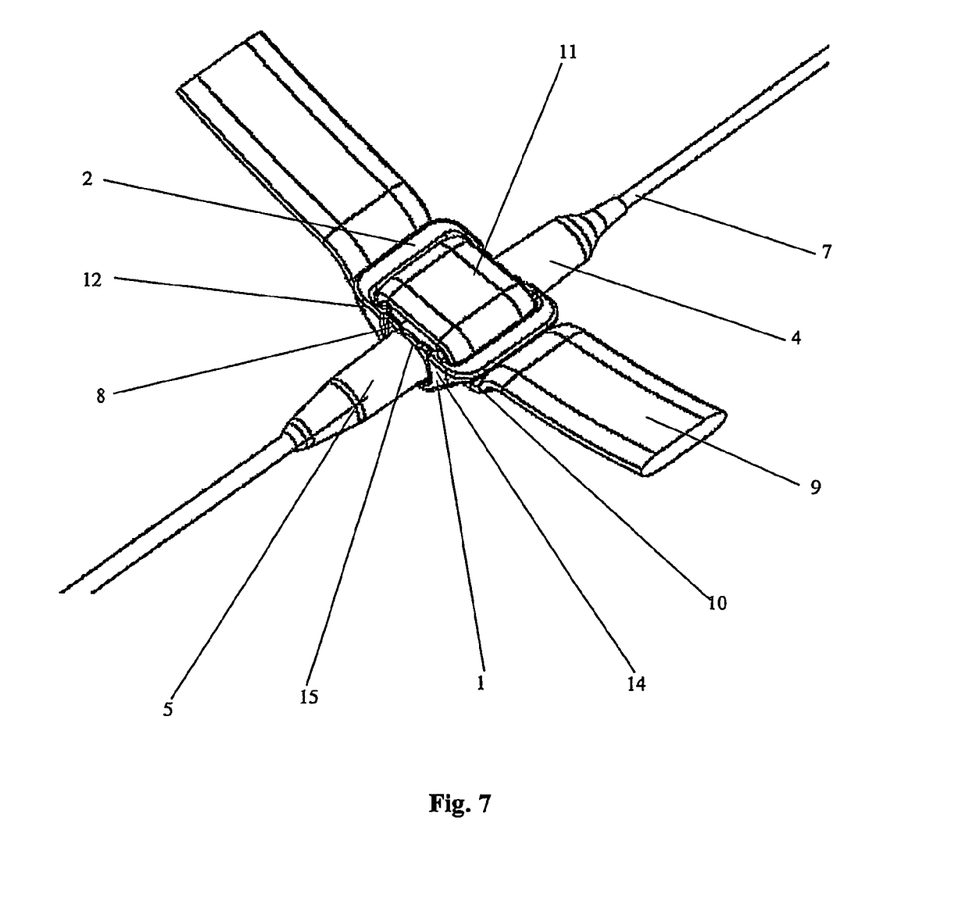
FIG. 7 is an inverted view of the first embodiment as shown in FIG. 6.
Figure 8:
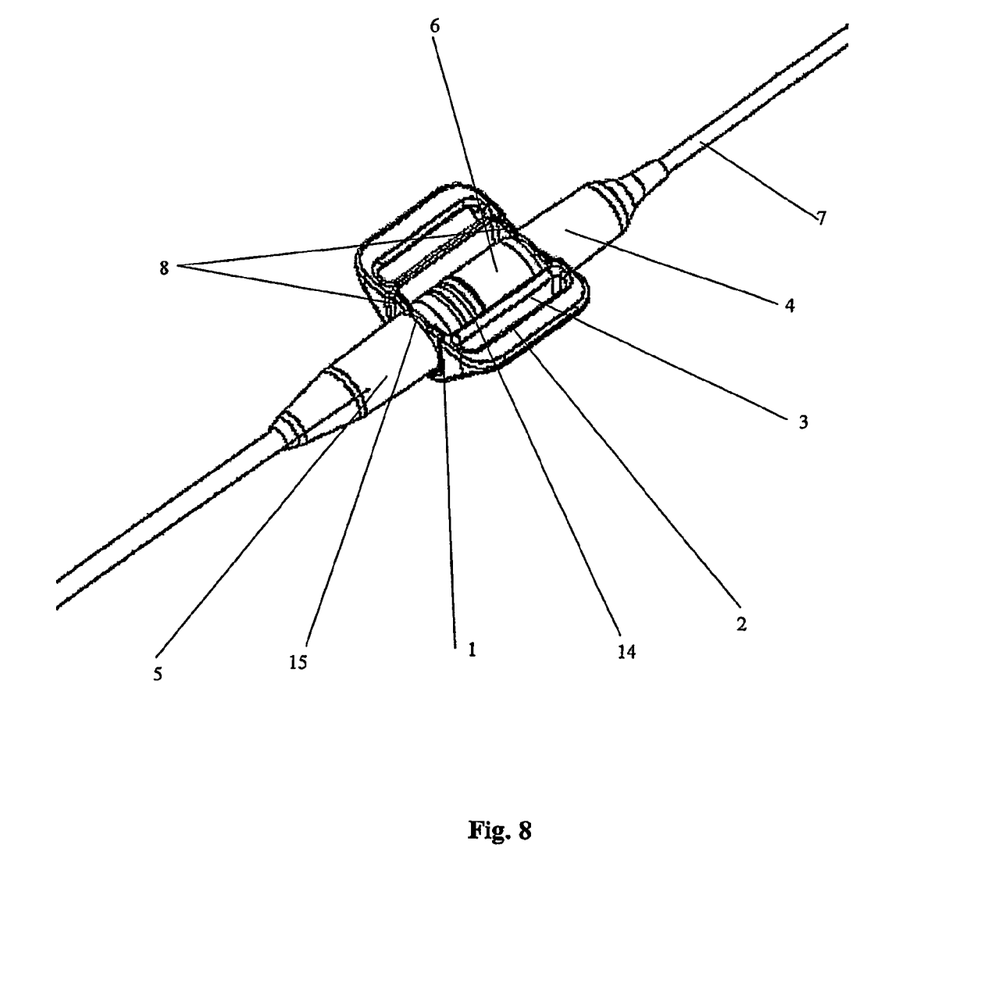
FIG. 8 is an alternate perspective view of the first embodiment as shown in FIG. 1.
Figure 9:
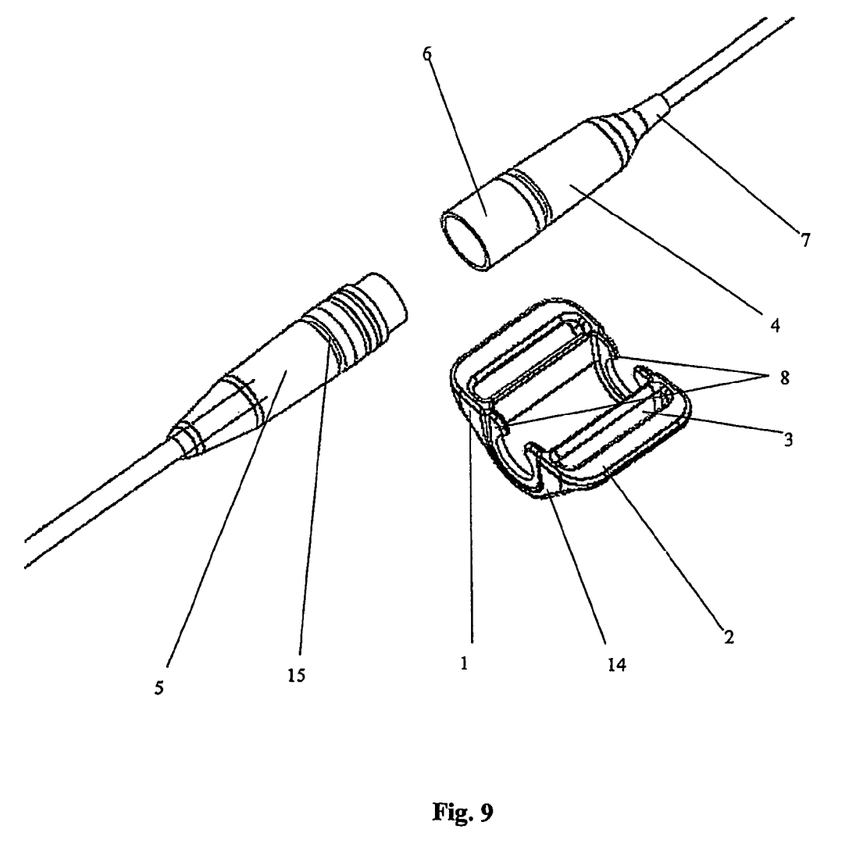
FIG. 9 is an exploded perspective view of the first embodiment as shown in FIG. 8.

FIGS. 1 to 9 depict a device 1 for restraining attached couplers 4 and 5 of a percutaneous lead assembly 7 adapted to extend through the skin layer of a patient. Assembly 7 preferably connects to an active implantable medical device (not shown), which it may also power.

Each of the couplers 4 and 5 also each include a slot 15. The device 1 comprises a resilient body 14, which is generally cradle shaped and adapted to receive the attached couplers 4 and 5. The resilient body 14 includes, at opposed ends, a circular flange 8. Each flange 8 functions as an engagement means and is adapted to engage the respective slots 15 positioned on the couplers 4 and 5. The resilient body 14 is capable of being deformed by the user and is resilient enough to return to its original shape without breaking the device 1 or the couplers 4 and 5. Preferably, the body 14 may be constructed of a plastic material.

The engagement of the flanges 8 within the slots 15, when in use, may allow the couplers 4 and 5 to be reliably secured within the resilient body 14 of device 1. The couplers 4 and 5, when inserted and secured within the device 1, resist mechanical separation by lateral pressure and also resist accidental disconnection from each other that may be caused by rubbing motion of the percutaneous lead.

Preferably, the device 1 may be bent or deformed by the fingers of the user to allow the insertion within the resilient body 14 of the couplers 4 and 5. When the device 1 is released by the user, the resilient body 14 returns to its original shape and substantially encapsulates the outer surface of couplers 4 and 5. The resilient body 14 is preferably rigid enough to prevent the couplers 4 and 5 from being disconnected by lateral forces applied to the percutaneous lead assembly 7 or the couplers 4 and 5.

The preferred cradle shape of the resilient body 14 substantially shields the attached couplers 4 and 5 thereby protecting them from wear and tear during the course of normal usage.

Preferably, the device 1 additionally includes extensions 2 mounted on alternate sides of body 14. These extensions 2 each include a gap 3 adapted to receive the flexible strip 9. Preferably, the flexible strip 9 may be thread over the upper surface 10 of the extension 2, then through gap 3 and across the underside region 11 of the device 1. The strip 9 is then passed up through the second gap 2 and over region 12. Preferably, the flexible strip 9 may be secured to the patient's skin or epidermis on either side of the device 1.

Preferably, in alternative embodiment the flexible strip 9 may be replaced with a Velcro™ strip and may be secured to skin or epidermis of a patient using a gauze dressing. The flexible strip 9 may also be affixed the skin of the patient using glue or a double sided hydrocolloid dressing such as Comfeel™ or Duoderm™. Once the flexible strip 9 is affixed to the skin layer of the patient the device 1 is effectively immobilised against the skin of the patient. When in use, the percutaneous lead assembly 7 and couplers 4 and 5 are restrained within the body 14 and the device 1 is itself restrained by the combination of the extensions 2, flexible strip 9, and the affixture of the flexible strip 9 to the epidermis. This feature, in effect immobilises or substantially restrains the entire arrangement from lateral movement.

Preventing lateral movement of device 1 may prevent damage from occurring to the percutaneous lead assembly 7 and/or the attached couplers 4 and 5. Additionally, preventing lateral movement of device 1 may minimize the risk of damage occurring to percutaneous lead assembly 7 and/or couplers 4 and 5 by normal wear and tear.

Additionally in this first embodiment, the resilient body 14 covers at least a portion of the percutaneous lead assembly 7 and the couplers 4 and 5. This feature may allow the device to at least partially protect the couplers 4 and 5 and percutaneous lead assembly 7 from additional accidental damage during use by means of physical separation. Also, the portion 11 of the flexible strip 9 functions to cover the lower surface of the device 1 and further shields the couplers 4 and 5, from damage.

Preferably, the device 1 may be constructed of any material that may allow the device 1 or the resilient body 14 to be deformed by the user and then, when released, return to its original shape. At least a small amount of rigidity is needed for the flanges 8 to properly engage slots 15 without allow accidental disconnection. One of the preferred construction materials of the device 1 is a blended polymer material of Acrylonitrile Butadiene Styrene ('ABS') and PolyCarbonate ('PC'), but the most preferred construction material is an Acetal Resin produced DuPont under the trade name Delrin™ 500P NC010.

Preferably, both couplers 4 and 5 include positioning markings (not shown). These positioning markers allow users or patients to align the markings and allow the couplers 4 and 5 to also be correctly aligned and connected. This feature may prevent the couplers 4 and 5 being inadvertently damaged by the user and also prevents incorrect polarity of the power supply being connected to the active implantable medical device (not shown).

Preferably, a locking catch 6 may be included within the percutaneous lead assembly 7 as a sleeve covering an outer portion of the male coupler 4. The locking catch 6 is preferably spring biased and is adapted to be rotated by the user to either selectively engage or disengage a corresponding portion of the female coupler 5. Preferably, the locking catch 6 may include a bayonet type fitting mechanism.

The locking catch 6 may also lockably engage the couplers 4 and 5 so as to resist disengagement by lateral pressure being applied to the couplers 4 and 5. This locking catch 6 is known in the prior art and is relatively common in the field of connectors and couplers. However, the locking catch 6 may fail, when used in conjunction with a percutaneous lead assembly 7. This is because the percutaneous lead assembly 7, when in use, may rub against the skin of the patient and this rubbing motion may accidentally induce rotation of the locking catch 6, which may, in turn, lead to accidental disengagement the couplers 4 and 5. This disengagement may also lead to a disconnection of power or signal for the active implanted medical device (not shown), which is not preferable when attaching the couplers 4 and 5 to each other.

In further embodiments, it is also possible to include with the device, an additional cover (not shown). This additional cover may be used to cover completely or partially the underside region 11 of the body 14 and in effect encapsulate the attached couplers 4 and 5. This provides the additional benefit may be that the couplers 4 and 5 and the percutaneous lead assembly 7 are additionally protected. Preferably, the cover may be secured to the underside region 11 by a snap lock mechanism.

The above descriptions detail only some of the embodiments of the present invention. Modifications may be obvious to those skilled in the art and may be made without departing from the scope and spirit of the present invention.

The term "comprising" (and its grammatical variations) as used herein is used in the inclusive sense of "having" or "including" and not in the exclusive sense of "consisting only of".

The invention claimed is:

1. A device for restraining couplers of a percutaneous lead assembly, comprising:
   a resilient body configured for being secured to a patient using a strap, the resilient body including
      a first flange and a second flange located, respectively, at first and second ends of the body, wherein the first and second flanges are configured to securely retain the couplers in the body when the couplers are forcibly pressed into openings formed by the flanges,
      a cover extending between the first and second flanges and shaped to cover the couplers when the couplers are retained in the body, and
      left and right sides of the body, each having an extension and gap extending between the first and second ends, wherein the strap is engaged with the resilient body by the strap passing over the right extension, through the right gap, beneath the cover, through the left gap and over the left extension;
   wherein when the couplers are retained in the resilient body and the device is configured for being secured to a patient via the strap, the connected couplers are protected by being disposed between the strap and the cover; and
   wherein the resilient body is configured such that the couplers are forcibly pressed into the openings before the strap can be passed over the respective extensions and through the gaps to dispose the couplers between the strap and the cover.

2. The device of claim 1, wherein the cover has a rounded profile when viewed from the ends and a straight profile when viewed from the sides,
   wherein the rounded profile provides a flexibility for the body necessary to enable the flange openings to open and close when the couplers are forcibly inserted therein to retain the couplers in the body, and
   wherein the straight profile provides a lateral strength in the body to resist disengagement of connected male and female portions of the couplers when tension is applied to the percutaneous lead assembly.

3. The device of claim 2, the resilient body having a top and a bottom, the bottom being shaped to enable the resilient body to be placed flush against a patient, and the top having the rounded shape of the cover.

4. The device of claim 3, wherein the resilient body is cradle-shaped and the rounded cover substantially shields and protects the couplers when the couplers are retained in the resilient body.

5. The device of claim 3, further including an additional cover configured for being snap-fit to the bottom so that the couplers are encapsulated between the cover and the additional cover.

6. The device of claim 1, wherein the resilient body includes a rounded and flexible cover joining first and second circular flanges so that when the couplers are being forcibly pressed into the flange openings the cover resiliently deforms to enable the flanges to be forcibly opened by the couplers, then closed to retain the couplers in the resilient body.

7. A method of assembly of a device for restraining and protecting a male coupler and a female coupler of a percutaneous lead, comprising:
   providing a resilient body having a first flange and a second flange located at a respective first and second end of the body, a protective and resilient cover extending from the first flange to the second flange, and a lengthwise extension and gap located at each one of a left and right side of the body and extending between the first and second ends;
   connecting the male coupler to the female coupler;
   after connecting the couplers, engaging the connected couplers to the resilient body including forcibly pressing the male coupler into an opening formed by the first flange and forcibly pressing the female coupler into an opening fowled by the second flange; and
   after the connected couplers are engaged to the resilient body, connecting the resilient body to a strap by passing the strap over the right extension, through the right gap, beneath the protective cover, through the left adjacent gap and then over the left extension;
   wherein when the device is fully assembled the male and female couplers are encapsulated by the strap, protective cover and left and right flanges;
   wherein the couplers are forcibly pressed into the openings before the strap can be passed over the respective extensions and through the gaps to dispose the couplers between the strap and the cover.

8. The method of claim 7, wherein the male coupler is removable from the female coupler by a locking catch requiring rotation of one of the male and female connectors relative to the other, whereby the encapsulation of the couplers prevents inadvertent rotation of one coupler relative to the other during a patient's use of the percutaneous lead.

\* \* \* \* \*